US00PP17647P2

(12) United States Plant Patent
Trees

(10) Patent No.: US PP17,647 P2
(45) Date of Patent: Apr. 24, 2007

(54) ***VERBENA* PLANT NAMED 'BALAZCORAL'**

(50) Latin Name: *Verbena×hybrida*
Varietal Denomination: Balazcoral

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 11 days.

(21) Appl. No.: 11/286,837

(22) Filed: Nov. 22, 2005

(51) Int. Cl.
*A01H 5/00* (2006.01)

(52) U.S. Cl. ..... Plt./308

(58) Field of Classification Search ..... Plt./308
See application file for complete search history.

(56) References Cited

PUBLICATIONS

European Plant Breeders' Rights application No. 2005/1959 filed Oct. 24, 2005.

*Primary Examiner*—Kent Bell
*Assistant Examiner*—Annette H Para
(74) *Attorney, Agent, or Firm*—Audrey Charles

(57) ABSTRACT

A new and distinct cultivar of *Verbena* plant named 'Balazcoral' characterized by its light salmon-colored flowers, medium green-colored foliage, good basal branching, and moderately vigorous, semi-trailing growth habit.

2 Drawing Sheets

Latin name of genus and species of plant claimed: *Verbena×hybrida.*
Variety denomination: 'Balazcoral'.

BACKGROUND OF THE INVENTION

The present invention relates to a new and distinct cultivar of *Verbena* plant botanically known as *Verbena×hybrida* and hereinafter referred to by the cultivar name 'Balazcoral'.

The new cultivar originated in a controlled breeding program in Arroyo Grande, Calif. during February 2003. The objective of the breeding program was the development of *Verbena* cultivars with attractive flower coloration, continuous flowering, small, dark green-colored foliage, and a moderately vigorous, trailing growth habit.

The female (seed) parent of the new cultivar was the proprietary *Verbena×hybrida* breeding selection designated BFP-1891, not patented, characterized by its rose red-colored flowers, dark green-colored foliage, and semi-upright growth habit. The male (pollen) parent of the new cultivar was 'Lan Rose', U.S. Plant Pat. No. 13,985, characterized by its rose pink-colored flowers, dark green-colored foliage, and trailing growth habit. The new *Verbena* was discovered and selected by the inventor as a single flowering plant within the progeny of the above stated cross-pollination during May 2003 in a controlled environment at Arroyo Grande, Calif.

Asexual reproduction of the new cultivar by terminal stem cuttings since May 2003 at Arroyo Grande, Calif. and West Chicago, Ill. has demonstrated that the new cultivar reproduces true to type with all characteristics, as herein discribed, firmly fixed and retained through successive generations of such asexual propagation.

SUMMARY OF THE INVENTION

The following characteristics of the new cultivar have been repeatedly observed and can be used to distinguish 'Balazcoral' as a new and distinct cultivar of *Verbena* plant:

1. Light salmon-colored flowers;
2. Medium green-colored foliage;
3. Good basal branching; and
4. Moderately vigorous, semi-trailing growth habit.

Plants of the new cultivar differ from plants of the female parent primarily in flower color and from plants of the male parent primarily in flower color and growth habit.

Of the many commercially available *Verbena* cultivars known to the inventor, the most similar in comparison to the new cultivar is 'Balazpeach', U.S. Plant patent application Ser. No. 10/742,088 abandoned. However, in side by side comparisons, plants of the new cultivar differ from plants of 'Balazpeach' in the following characteristics:

1. Plants of the new cultivar are shorter than plants of 'Balazpeach';
2. Plants of the new cultivar are wider than plants of 'Balazpeach'; and
3. Plants of the new cultivar have a lighter flower color than plants of 'Balazpeach'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balazcoral'. The plants were grown in 10 cm pots for 12 weeks in a greenhouse at West Chicago, Ill.

DETAILED BOTANICAL DESCRIPTION

Figure 1:
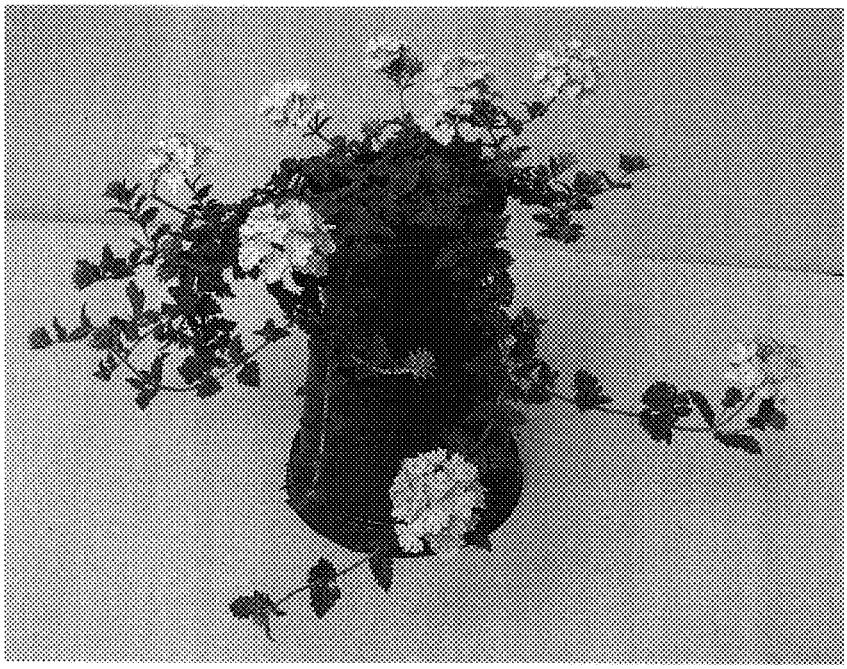
FIG. 1 illustrates a side view of the overall growth and flowering habit of 'Balazcoral'.
Figure 2:
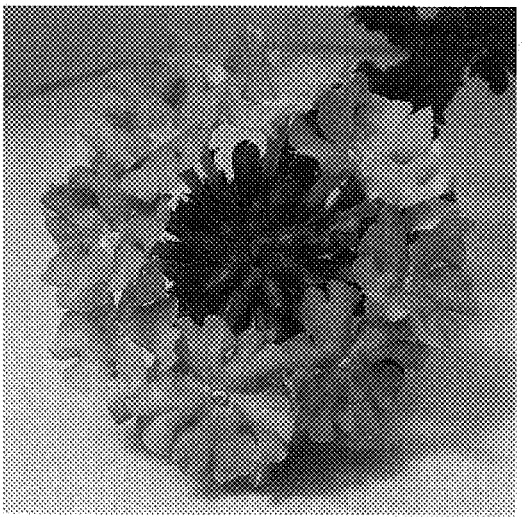
FIG. 2 illustrates a close-up view of a single inflorescence of 'Balazcoral' with some flowers first to open.
Figure 3:
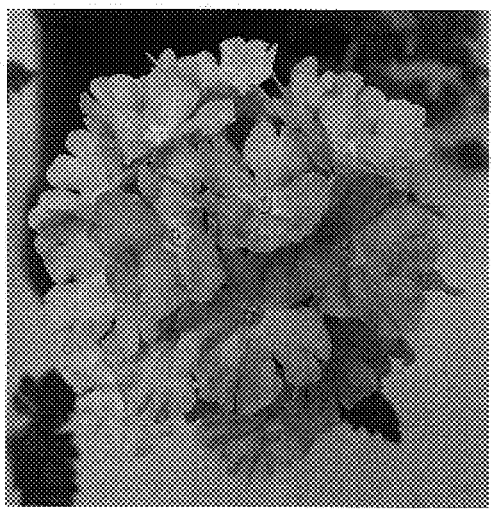
FIG. 3 illustrates a close-up view of a single inflorescence of 'Balazcoral' with all flowers first open.
Figure 4:
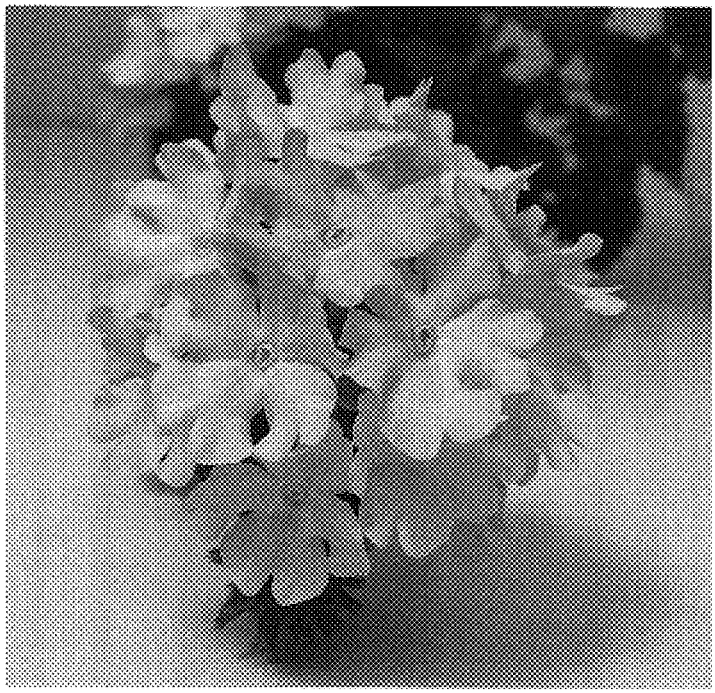
FIG. 4 illustrates a close-up view of a single inflorescence of 'Balazcoral' with all flowers fully open.
Figure 5:
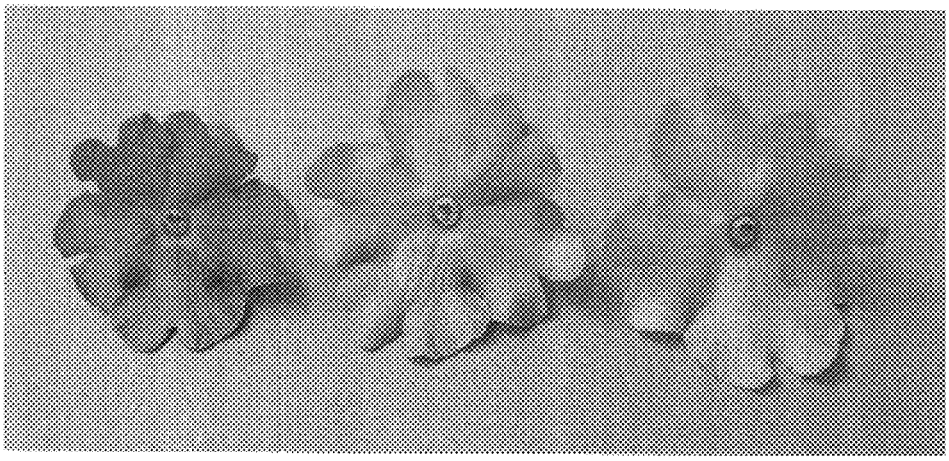
FIG. 5 illustrates three single flowers of 'Balazcoral' showing color change from first open on left to fully open on right.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 18, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 12 weeks utilizing a soilless growth medium. Greenhouse temperatures were maintained at approximately 70° F. to 80° F. (21° C. to 26° C.) during the day and approximately 62° F. to 65° F. (17° C. to 18° C.) during the night. Greenhouse light levels of 5,000 to 8,000 footcandles were maintained during the day.

Botanical classification: *Verbena×hybrida* cultivar Balazcoral.

Parentage:

*Female parent.*—Proprietary *Verbena×hybrida* breeding selection designated BFP-1891, not patented.

*Male parent.*—'Lan Rose', U.S. Plant Pat. No. 13,985.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous.

*Rooting habit.*—Freely branching.

Plant description:

*Crop time.*—Approximately 5 to 7 weeks from a rooted cutting.

*Growth habit and general appearance.*—Moderately vigorous, semi-trailing.

*Size.*—Height from soil level to top of plant plane: Approximately 6.1 cm. Width: Approximately 74.2 cm.

*Branching habit.*—Freely basal branching. Approximately 6 main branches per plant with lateral branches potentially forming at every node.

*Branch.*—Shape: Square in cross section. Strength: Strong. Length: Approximately 38.2 cm. Diameter: Approximately 2.0 mm. Texture: Densely hispid. Color: 144B. Internode length at center of branch: Approximately 3.2 cm.

*Foliage.*—Number of leaves per main branch: Approximately 22. Fragrance: None. Form: Simple. Arrangement: Opposite. Aspect: At acute angle to stem. Shape: Ovate. Margin: Dentate. Apex: Acuminate. Base: Truncate. Venation pattern: Pinnate. Length of mature leaf: Approximately 4.0 cm. Width of mature leaf. Approximately 2.8 cm. Texture of upper surface: Densely pubescent. Texture of lower surface: Moderately pubescent and densely pubescent along veins. Color of upper surface of young and mature foliage: 137A with venation of 143C. Color of lower surface of young and mature foliage: 138B with venation of 144D. Petiole length: Approximately 3.1 mm. Petiole diameter: Approximately 1.4 mm. Petiole texture: Hispid. Petiole color: 144D.

Flowering description:

*Flowering habit.*—'Balazcoral' is freely flowering under outdoor growing conditions with substantially continuous blooming from spring through autumn and year round in greenhouse environment.

*Time to first flower.*—Approximately 11 weeks from sticking of an unrooted cutting.

*Lastingness of individual bloom.*—Approximately 5 to 7 days.

Inflorescence description:

*Type.*—Corymb. Quantity per plant: Approximately 5 at 12 weeks. Length/Height: Approximately 4.0 cm. Width: Approximately 6.1 cm. Quantity of fully opened flowers per inflorescence at any one time: Approximately 22. Fragrance: None.

*Peduncle.*—Strength: Strong. Aspect: Erect. Length: Approximately 2.2 cm. Diameter: Approximately 1.5 mm. Texture: Densely pubescent. Color: 144B.

Flower description:

*Type.*—Sessile, salverform. Fragrance: None.

*Bud rate of opening.*—Generally takes 3 to 5 days for bud to progress from first color to fully open flower.

*Bud just before opening.*—Shape: Elongated, globular. Length: Approximately 4.3 mm. Diameter: Approximately 3.1 mm. Color: Closest to 48D.

*Corolla.*—Shape: Round. Diameter: Approximately 2.2 cm. Depth: Approximately 3.8 mm.

*Petals.*—Quantity: 5 fused at base forming a tube. Appearance: Dull. Aspect: Downturning along margin. Shape: Obovate. Apex: Emarginate. Margin: Entire. Texture of upper surface: Glabrous. Texture of lower surface: Sparsely pubescent. Length of upper petal from tube. Approximately 9.9 mm. Width of upper petal: Approximately 9.0 mm. Length of lateral petal from tube: Approximately 9.0 mm. Width of lateral petal: Approximately 1.0 cm. Length of lower petal from tube: Approximately 9.0 mm. Width of lower petal: Approximately 7.0 mm. Color of upper surface when just opening: 52B. Color of upper surface when first open: Closest to 48D. Color of upper surface when fully open: Closest to between 158C and 158D. Color of lower surface when just opening: Between 38A and 38B. Color of lower surface when first open: Closest to 27D. Color of lower surface when fully open: Closest to 159C. Whiskers of 144D surround the opening of the corolla tube.

*Corolla tube.*—Length: Approximately 2.1 cm. Diameter at corolla: Approximately 2.5 mm. Diameter at base: Approximately 1.9 mm. Texture of inner surface: Densely pubescent. Texture of outer surface: Moderately pubescent. Color of inner and outer surfaces: 144D.

*Calyx.*—Shape: Tubular, with 5 acute tips. Length/Depth: Approximately 1.3 cm. Width: Approximately 1.8 mm.

*Sepals.*—Quantity per flower: 5. Shape: Lanceolate. Apex: Acute. Margin: Entire. Sepal length: Approximately 1.3 cm. Sepal width: Approximately 1.0 mm. Texture of upper or inner surface: Glabrous. Texture of lower or outer surface: Densely pubescent with a mixture of glandular and non-glandular hairs. Gland color: Colorless, translucent. Color of upper or inner surface: 144A. Color of lower or outer surface: 144C. Stipule shape: Lanceolate. Stipule apex: Acuminate: Stipule length: Approximately 5.0 mm. Stipule width at base: Approximately 1.2 mm. Stipule texture of upper or inner surface: Densely pubescent. Stipule texture of lower or outer surface: Glabrous. Stipule color: 144A.

*Reproductive organs.*—Androecium: Stamen quantity: 4. Stamen length: Approximately 2.0 mm. Anther shape: Ovate, bilobed. Anther length: Approximately 1.0 mm. Anther color: 143B. Pollen amount: Abundant. Pollen color 150D. Gynoecium: Pistil quantity: One per flower. Pistil length: Approximately 2.0 cm. Stigma shape: Funnel. Stigma length: Approximately 1.5 mm. Stigma color: 143B. Style length: Approximately 1.7 cm. Style color: 150B. Ovary diameter: Approximately 1.5 mm. Ovary texture: Glabrous. Ovary color: 144B.

Seed and fruit production: Neither seed nor fruit production has been observed.

Disease and pest resistance: Resistance to pathogens and pests common to *Verbena* has not been observed.

What is claimed is:

1. A new and distinct cultivar of *Verbena* plant named 'Balazcoral', substantially as herein shown and described.

* * * * *